United States Patent

Kevehazi

[11] Patent Number: 6,064,425
[45] Date of Patent: May 16, 2000

[54] SYSTEM, AND METHOD AND DEVICE FOR PERSONALIZED TOOTHBRUSH

[76] Inventor: Laura Mann Kevehazi, 15 Schaham Street, Ramat Efal, Israel

[21] Appl. No.: 08/997,657

[22] Filed: Dec. 23, 1997

[30] Foreign Application Priority Data

Dec. 29, 1996 [IL] Israel ......................................... 119926

[51] Int. Cl.[7] .............................. H04N 7/18; A61C 9/00
[52] U.S. Cl. ............................. 348/61; 433/214; 433/215
[58] Field of Search .......................... 348/61, 66; 382/152, 382/128, 154; 433/214, 215, 223, 72

[56] References Cited

U.S. PATENT DOCUMENTS 3,650,031  3/1972  Shilliday ................................... 433/214
5,846,081  12/1998  Bushway ................................... 433/215

*Primary Examiner*—Bryan Tung
*Assistant Examiner*—Allen Wong
*Attorney, Agent, or Firm*—Edwin D. Schindler

[57] ABSTRACT

A system for matching the shape of a toothbrush to the occlusal (chewing surface of the teeth) regarding both size and shape (angles of the chewing surface), and to a device implementing the system. The system provides a variety of differently shaped toothbrushes, as well as the means for choosing the closest possible match between the size and shape of the posterior teeth and the brush. The device comprises: 1 a housing provided with means for placing the imprint thereon; 2 a sensor adapted to scan the imprint; 3 and display means for displaying the result of the scanning.

8 Claims, 1 Drawing Sheet

SYSTEM, AND METHOD AND DEVICE FOR PERSONALIZED TOOTHBRUSH

FIELD OF INVENTION

The present invention relates to a system for matching the shape of a toothbrush to the oclusal (chewing surface of the teeth) regarding both size and shape (angles of the chewing surface), and to a device implementing the system.

The system provides a variety of differently shaped toothbrushes, as well as the means for choosing the closest possible match between the size and shape of the posterior teeth and the brush—therefore meeting the requirements of close contact between the bristles of the toothbrush and pits and fissures of the chewing surface.

BACKGROUND OF THE INVENTION

A wide variety of toothbrushes on the market today differ in bristle length, hardness, angle and shape of the handle and the like. Up to now no individually fitted toothbrushes have been available on the market. As opposed to the anterior teeth which are flat and therefore easier to brush the oclusal surface of the posterior teeth with its pits and fissures represents the main starting point of dental decay (cavities). The importance of close contact between the brush and the oclusal surface is thus obvious.

SUMMARY OF THE INVENTION

The invention relates to a system for optimizing a toothbrush supplied to a customer according to the chewing surface (both shape and size).

The system comprises the following steps:

obtaining an imprint of the chewing surface of a person in a suitable sterile medium such as wax (sterilized, individually packed and disposable);

removing the imprint from the mouth and transferring it to an examining and scanning device;

the device—evaluates the imprint regarding size and shape, and indicates which type of toothbrush from a selection of different shapes of toothbrushes is suitable. Therefore, the best approximated match for that specific customer is acquired.

The invention further relates to a device adopted to scan and evaluate the imprint which comprises: 1 a housing provided with means for placing the imprint thereon; 2 a sensor adapted to scan the imprint; 3 and display means for displaying the result of the scanning.

In practice, the individual bite impression can be obtained by using a horse shoe shaped form containing a suitable material such as wax which is introduced between the teeth of the customer. The person bites on it, removes it from his/her mouth, inserts it into the brush match device which after evaluating the imprint provides a numeric answer.

The evaluation of the imprint is based on electronic scanning of parameters, established beforehand, and relates it to the available models of toothbrushes.

The numeric answer indicates which specific toothbrush is appropriate and matches the customers anatomic tooth and mouth shape.

SHORT DESCRIPTION OF DRAWINGS

The invention will now be described with reference to the annexed drawings in which.

DESCRIPTION OF PREFERRED EMBODIMENT

Figure 1:
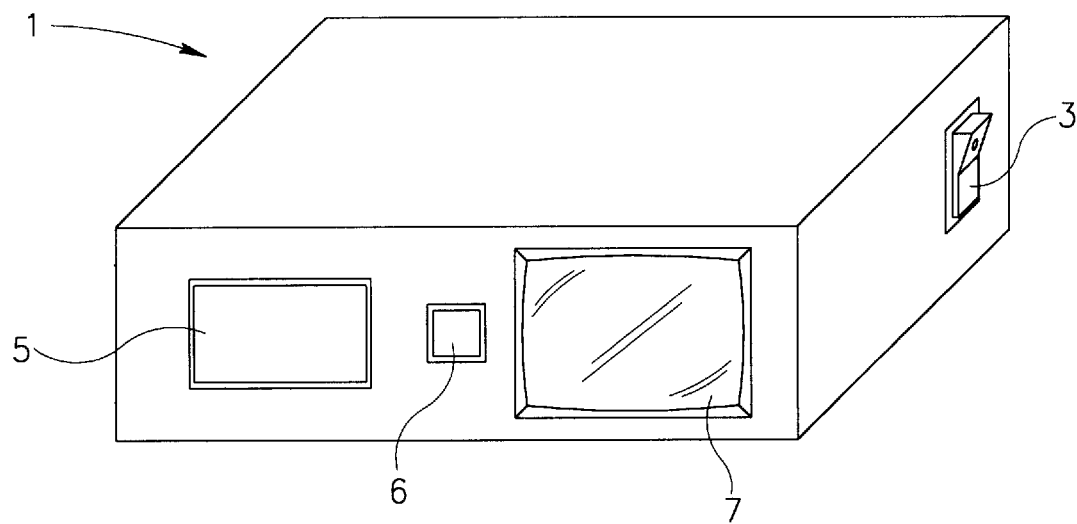
FIG. 1 is a schematical illustration of the device.
Figure 2:
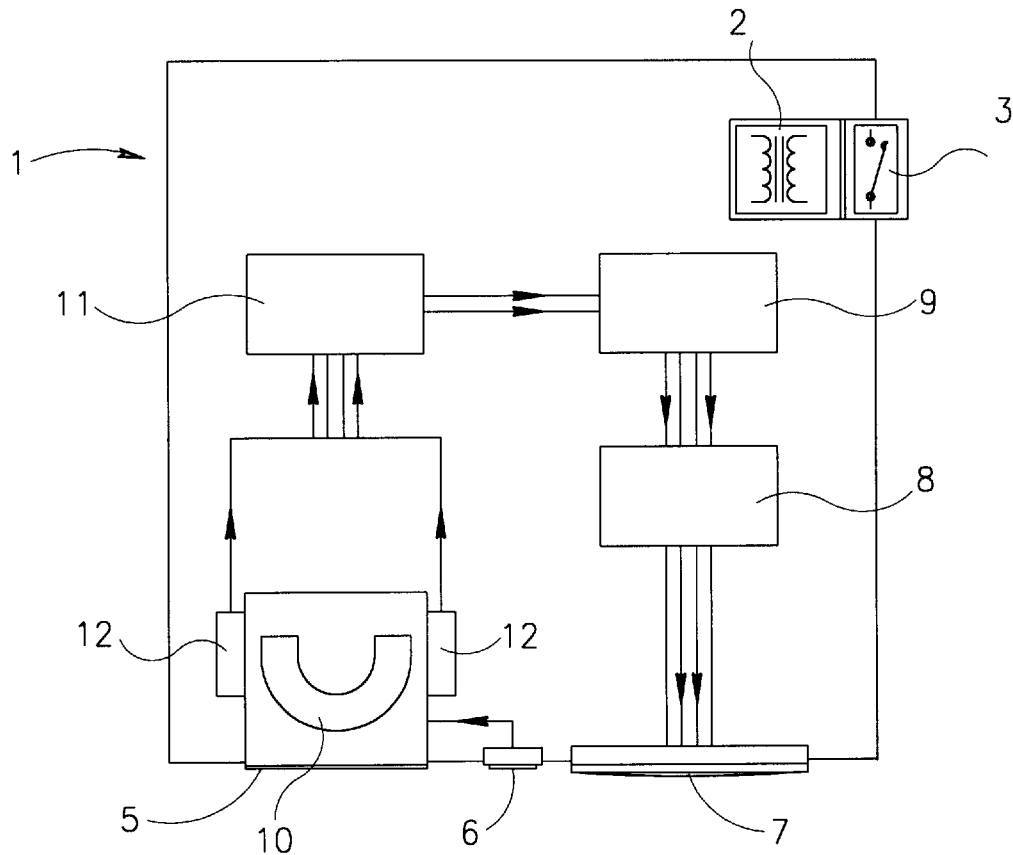
FIG. 2 illustrates the various components of the device.

The device comprises housing 1 provided with external on/off switch 3. A drawer 5 is provided for placing thereon the imprint 10 for scanning and evaluation. Push-button 6 activates drawer 5 for placing the imprint 10 thereon. Screen 7 would display the results of the scanning. Imprint 10 is placed on or in drawer 5. Scanning means 12 would analyze the tooth impression by one of the following methods:

1. Infra red sensors (I.R.);
2. Differential resistance (Resistors);
3. Three-dimensional video analyzers based on two cameras and an image data microprocessor card;
4. Volume displacement/impedance sensors.

Any of the above methods could be used and provide the required data to the Amplifier 11, which in turn would transfer it to the reference to data base (memory) 9 for evaluation. Once the evaluation is completed the result would be forwarded to driver 8 to be displayed on screen 7.

It is clear that the number of different toothbrushes is limited being a matter of practical choice, but the set of toothbrushes which accompanies the evaluating device, includes sufficient variations (assuming 5–10 types) meeting customers requirements.

This provides the customer with a toothbrush that enables him/her to achieve by far superior brushing results in terms of plaque removing action lowering his/her dental decay risk.

I claim:

1. A system for optimizing a toothbrush supplied to a customer according to the chewing surface which comprises the steps of:

a. obtaining an imprint of the chewing surface of a person in a suitable sterile medium, b. removing the imprint from the mouth and transferring it to an examining and scanning device;

c. evaluating the imprint regarding size and shape, and indicating which type of toothbrush from a selection of different shapes of toothbrushes is suitable.

2. A system for optimizing a toothbrush, comprising a device adapted to scan and evaluate an imprint, which comprises: a housing provided with means for placing the imprint thereon, scanning means for scanning the imprint for selecting a feature of a toothbrush, a memory unit including means for evaluating the scanned imprint and display means for displaying the features of the toothbrush selected on the basis of the scanned imprint.

3. A system for optimizing a toothbrush as claimed in claim 1 where the bite impression is obtained by a horseshoe shaped form.

4. A system for optimizing a toothbrush as claimed in claim 1 where said horseshoe form is filled with wax.

5. A system for optimizing a toothbrush as claimed in claim 1 where said sensor is an infra red (I.R.) sensor.

6. A system for optimizing a toothbrush as claimed in claim 1 where said sensor is a differential resistor.

7. A system for optimizing a toothbrush as claimed in claim 1 where said sensor is a three dimensional video based on two cameras and an image data microprocessor card.

8. A system for optimizing a toothbrush as claimed in claim 1 where said sensor is volume displacement/impedance sensors.

* * * * *